United States Patent
Beaurepaire et al.

(10) Patent No.: US 12,332,061 B2
(45) Date of Patent: Jun. 17, 2025

(54) SYSTEMS AND METHODS FOR DETERMINING A ROUTE FOR MOOD IMPROVEMENT

(71) Applicant: HERE GLOBAL B.V., Eindhoven (NL)

(72) Inventors: Jerome Beaurepaire, Nantes (FR); Gianpietro Battistutti, Berlin (DE)

(73) Assignee: HERE GLOBAL B.V., Eindhoven (NL)

( * ) Notice: Subject to any disclaimer, the term of this patent is extended or adjusted under 35 U.S.C. 154(b) by 318 days.

(21) Appl. No.: 17/880,604

(22) Filed: Aug. 3, 2022

(65) Prior Publication Data
US 2024/0044654 A1    Feb. 8, 2024

(51) Int. Cl.
  G01C 21/34    (2006.01)
  A61B 5/16    (2006.01)
  G01C 21/36    (2006.01)
  G05D 1/00    (2024.01)

(52) U.S. Cl.
  CPC .......... *G01C 21/3407* (2013.01); *A61B 5/165* (2013.01); *G01C 21/3446* (2013.01); *G01C 21/3605* (2013.01); *G05D 1/0212* (2013.01)

(58) Field of Classification Search
  None
  See application file for complete search history.

(56) References Cited

U.S. PATENT DOCUMENTS

| | | | |
|---|---|---|---|
| 8,364,395 B2 | 1/2013 | French et al. | |
| 9,466,161 B2 | 10/2016 | Ricci | |
| 9,547,309 B2* | 1/2017 | Ross | G06Q 10/06 |
| 9,792,084 B2* | 10/2017 | Vartakavi | G06F 16/639 |
| 10,150,351 B2 | 12/2018 | Lin et al. | |
| 2016/0089954 A1* | 3/2016 | Rojas Villanueva | B60H 1/00742 701/36 |
| 2017/0059339 A1* | 3/2017 | Sugawara | G01C 21/3484 |
| 2023/0410423 A1* | 12/2023 | Fasola | G01S 17/931 |

OTHER PUBLICATIONS

Kariryaa et al., Activity and mood-based routing for autonomous vehicles, 2008, 5.

* cited by examiner

*Primary Examiner* — James J Lee
*Assistant Examiner* — Elizabeth Galyn Martinez
(74) *Attorney, Agent, or Firm* — Jason Wejnert; HERE GLOBAL B.V.

(57) ABSTRACT

Systems and methods for determining a route for mood improvement are provided. For example, a method of determining a route for mood improvement includes determining a mood of an individual. The method also includes receiving a destination as an input. The method also includes determining a route from a current location of the individual to the destination via a plurality of road segments for improving the mood of the individual.

18 Claims, 7 Drawing Sheets

SYSTEMS AND METHODS FOR DETERMINING A ROUTE FOR MOOD IMPROVEMENT

TECHNICAL FIELD

The present disclosure relates generally to determining routes, and more specifically to systems and methods for determining a route for improving the mood of an individual.

BACKGROUND

The term autonomous vehicle refers to a vehicle including automated mechanisms for performing one or more human operated aspects of vehicle control. As autonomous vehicles are adopted, several benefits may be realized. Vehicle collisions may be reduced because computers can perform driving tasks more consistently and make fewer errors than human operators. Traffic congestion may be alleviated because autonomous vehicles observe specified gaps between vehicles, preventing stop and go traffic. Despite the benefits of utilizing an autonomous vehicle, there are still challenges in maximizing individual experiences based on the various stressors in modern day life.

BRIEF SUMMARY

The present disclosure overcomes the shortcomings of prior technologies. In particular, a novel approach for determining a route for mood improvement is provided, as detailed below.

In accordance with an aspect of the disclosure, a method for determining a route for mood improvement is provided. The method includes determining a mood of an individual. The method also includes receiving a destination as an input. The method also includes determining a route from a current location of the individual to the destination via a plurality of road segments for improving the mood of the individual.

In accordance with another aspect of the disclosure, an apparatus for determining a route for mood improvement is provided. The apparatus includes a processor. The apparatus also includes a memory comprising computer program code for one or more programs. The memory and the computer program code are configured to cause the processor of the apparatus to determine a mood of an individual. The computer program code is further configured to cause the processor of the apparatus to receive a destination as an input. The computer program code is further configured to cause the processor of the apparatus to determine a route from a current location of the individual to the destination via a plurality of road segments for improving the mood of the individual.

In accordance with another aspect of the present disclosure, a non-transitory computer-readable storage medium is provided. The non-transitory computer-readable storage medium includes one or more sequences of one or more instructions for execution by one or more processors of a device. The one or more instructions which, when executed by the one or more processors, cause the device to determine a mood of an individual. The one or more instructions further cause the device to receive a destination as an input. The one or more instructions further cause the device to determine a route from a current location of the individual to the destination via a plurality of road segments for improving the mood of the individual.

In addition, for various example embodiments, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment.

For various example embodiments, the following is also applicable: a method comprising facilitating access to at least one interface configured to allow access to at least one service, the at least one service configured to perform any one or any combination of network or service provider methods (or processes) disclosed in this application.

For various example embodiments, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment, and/or at least one signal resulting from one or any combination of methods (or processes) disclosed in this application as relevant to any embodiment.

For various example embodiments, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment, and/or at least one signal resulting from one or any combination of methods (or processes) disclosed in this application as relevant to any embodiment.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of the claims.

Still other aspects, features, and advantages are readily apparent from the following detailed description, simply by illustrating a number of particular embodiments and implementations. The drawings and description are to be regarded as illustrative in nature, and not as restrictive.

BRIEF DESCRIPTION OF THE DRAWINGS

The embodiments are illustrated by way of example, and not by way of limitation, in the figures of the accompanying drawings.

DESCRIPTION OF SOME EMBODIMENTS

Examples of a method, apparatus, and a non-transitory computer-readable storage medium for determining a route for mood improvement are disclosed. In the following description, for the purposes of explanation, numerous specific details are set forth in order to provide a thorough understanding of the embodiments. It is apparent, however, to one skilled in the art that the embodiments may be practiced without these specific details or with an equivalent arrangement. In other instances, well-known structures and devices are shown in block diagram form in order to avoid unnecessarily obscuring the embodiments.

Figure 1:
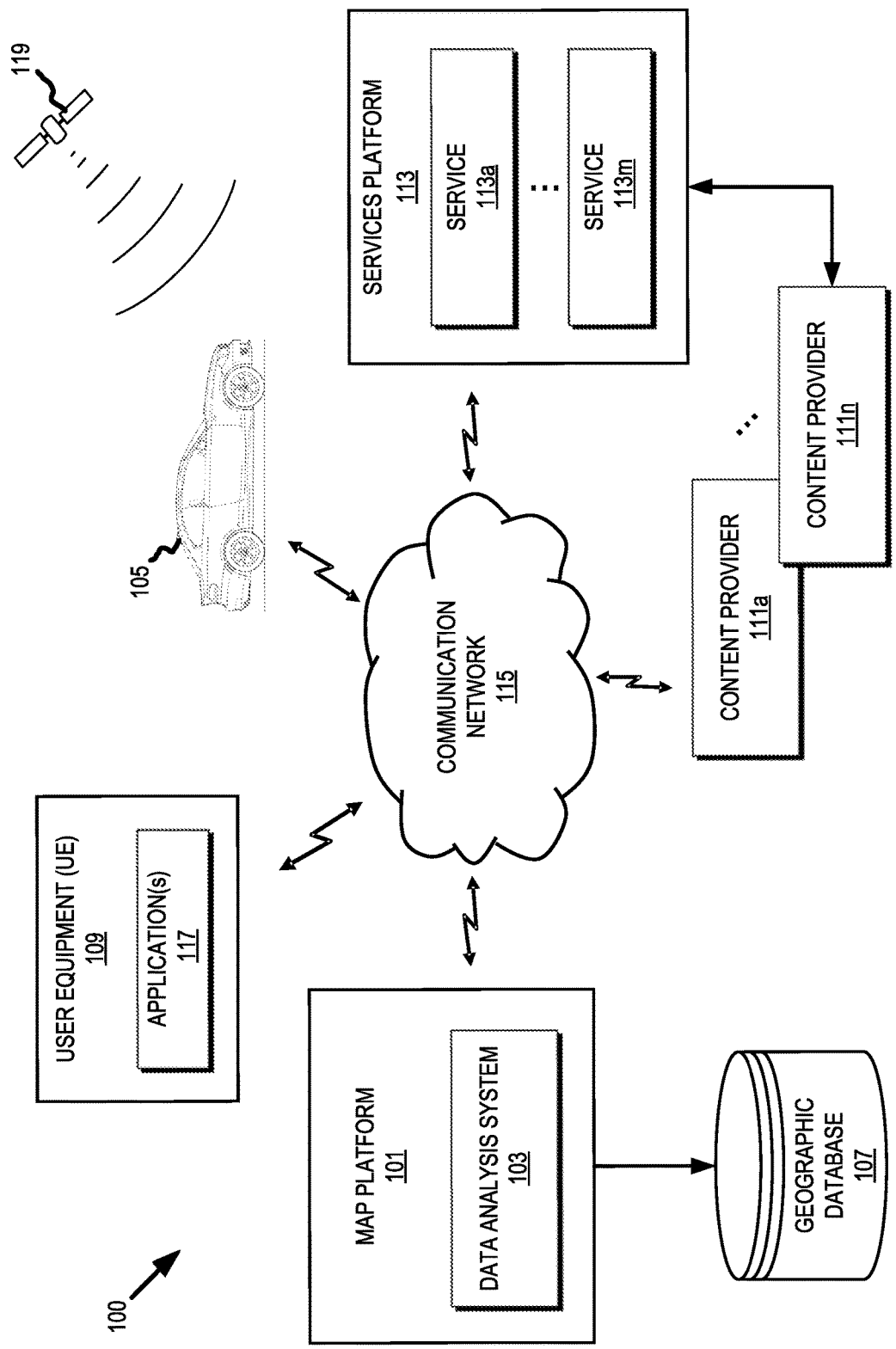
FIG. 1 is a diagram of a system capable of determining a route for mood improvement, in accordance with aspects of the present disclosure.

FIG. 1 is a diagram of a system 100 capable of determining a route for mood improvement, according to one embodiment. In one example, the system 100 is configured to determine a baseline mood of an individual. In one example, the system 100 is configured to determine a baseline mood of the individual based on analysis of mobility patterns of the individual over a predefined period of time. For example, they system 100 may be configured to determine the days of the week that the individual is working based on analysis of the mobility patterns. In one scenario, the system 100 may be configured to determine a baseline mood of the individual for each day of the week. For example, the system 100 may determine that the individual's baseline mood is higher on days when the individual is not at a place of work compared to the days when the individual is at a place of work.

In one embodiment, the mood of the individual may be based on one or more emotions that the individual has experienced in a given period of time. The one or more may be a mix of positive and negative emotions that cause physiological changes in the individual that are detectable by one or more sensors. In one example, the system 100 is configured to receive one or more measurements, captured via one or more sensors, that enable the system 100 to determine a current mood of the individual. The one or more measurements may be tied to blood pressure, temperature, movement data, etc. In one example, an individual may feel stress because of any number of factors in the given period of time and the system 100 may be configured to determine that the individual is in a bad mood. In this example, the system 100 may determine, based on one or more measurements, that the individual's current mood is below the individual's baseline mood. Continuing with this example, the system 100 may receive a request to transport the individual from a current location to a destination and determine one or more routes from the current location (e.g., the individual's workplace) to the destination (e.g., the individual's home) that may improve the mood of the individual by having the individual travel along one of those determined routes in a given vehicle selected by the system 100.

The vehicle may be a standard gasoline powered vehicle, a hybrid vehicle, an electric vehicle, a fuel cell vehicle, and/or any other mobility implement type of vehicle. The vehicle includes parts related to mobility, such as a powertrain with an engine, a transmission, a suspension, a driveshaft, and/or wheels, etc. The vehicle may be a manually controlled vehicle, semi-autonomous vehicle (e.g., some routine motive functions, such as parking, are controlled by the vehicle), or an autonomous vehicle (e.g., motive functions are controlled by the vehicle without direct driver input).

The autonomous level of a vehicle can be a Level 0 autonomous level that corresponds to no automation for the vehicle, a Level 1 autonomous level that corresponds to a certain degree of driver assistance for the vehicle, a Level 2 autonomous level that corresponds to partial automation for the vehicle, a Level 3 autonomous level that corresponds to conditional automation for the vehicle, a Level 4 autonomous level that corresponds to high automation for the vehicle, a Level 5 autonomous level that corresponds to full automation for the vehicle, and/or another sub-level associated with a degree of autonomous driving for the vehicle. In one embodiment, user equipment (e.g., a mobile phone, a portable electronic device, etc.) may be integrated in the vehicle, which may include assisted driving vehicles such as autonomous vehicles, highly assisted driving (HAD), and advanced driving assistance systems (ADAS). Any of these assisted driving systems may be incorporated into the user equipment. Alternatively, an assisted driving device may be included in the vehicle.

The term autonomous vehicle may refer to a self-driving or driverless mode in which no passengers are required to be on board to operate the vehicle. An autonomous vehicle may be referred as a robot vehicle or an automated vehicle. The autonomous vehicle may include passengers, but no driver is necessary. These autonomous vehicles may park themselves or move cargo between locations without a human operator. Autonomous vehicles may include multiple modes and transition between the modes. The autonomous vehicle may steer, brake, or accelerate and respond to lane marking indicators (lane marking type, lane marking intensity, lane marking color, lane marking offset, lane marking width, or other characteristics) and driving commands or navigation commands.

In one embodiment, the vehicle may be an HAD vehicle or an ADAS vehicle. An HAD vehicle may refer to a vehicle that does not completely replace the human operator. Instead, in a highly assisted driving mode, the vehicle may perform some driving functions and the human operator may perform some driving functions. Vehicles may also be driven in a manual mode in which the human operator exercises a degree of control over the movement of the vehicle. The vehicles may also include a completely driverless mode. Other levels of automation are possible. The HAD vehicle may control the vehicle through steering or braking in response to the on the position of the vehicle and may respond to lane marking indicators (lane marking type, lane marking intensity, lane marking color, lane marking offset, lane marking width, or other characteristics) and driving commands or navigation commands. Similarly, ADAS vehicles include one or more partially automated systems in which the vehicle alerts the driver. The features are designed to avoid collisions automatically. Features may include adaptive cruise control, automate braking, or steering adjustments to keep the driver in the correct lane. ADAS vehicles may issue warnings for the driver based on the position of the vehicle or based on the lane marking indicators (lane marking type, lane marking intensity, lane marking color, lane marking offset, lane marking width, or other characteristics) and driving commands or navigation commands.

In one example, the system 100 may be configured to determine a route for improving the mood of the individual based on the shortest route that will enable an individual to reach a target mood. In another example, the system 100 may be configured to determine a route for improving the mood of the individual based on dynamic conditions (e.g., weather, traffic, events, etc.) and the route that will most likely enable an individual to reach a target mood. In one example, the system 100 may be configured to update a route based on the reaching a target mood. Based on the route determined and selected for improving the mood of the individual, the system 100 may be configured to determine an autonomous vehicle for transporting the individual from a current location to a destination.

Referring to FIG. 1, the map platform 101 can be a standalone server or a component of another device with connectivity to the communication network 115. For example, the component can be part of an edge computing network where remote computing devices (not shown) are installed along or within proximity of a given geographical area.

The communication network 115 of the system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, fifth generation mobile (5G) networks, code division multiple access (CDMA), wideband code division multiple access (WCDMA), wireless fidelity (Wi-Fi), wireless LAN (WLAN), Bluetooth®, Internet Protocol (IP) data casting, satellite, mobile ad-hoc network (MANET), and the like, or any combination thereof.

In one embodiment, the map platform 101 may be a platform with multiple interconnected components. The map platform 101 may include multiple servers, intelligent networking devices, computing devices, components and corresponding software for generating information for determining a route for mood improvement or other map functions. In addition, it is noted that the map platform 101 may be a separate entity of the system 100, a part of one or more services 113*a*-113*m* of a services platform 113.

The services platform 113 may include any type of one or more services 113*a*-113*m*. By way of example, the one or more services 113*a*-113*m* may include weather services, mapping services, navigation services, travel planning services, notification services, social networking services, content (e.g., audio, video, images, etc.) provisioning services, application services, storage services, information for determining a route for mood improvement, location-based services, news services, etc. In one embodiment, the services platform 113 may interact with the map platform 101, and/or one or more content providers 111*a*-111*n* to provide the one or more services 113*a*-113*m*.

In one embodiment, the one or more content providers 111*a*-111*n* may provide content or data to the map platform 101, and/or the one or more services 113*a*-113*m*. The content provided may be any type of content, mapping content, textual content, audio content, video content, image content, etc. In one embodiment, the one or more content providers 111*a*-111*n* may provide content that may aid in determining a route for mood improvement according to the various embodiments described herein. In one embodiment, the one or more content providers 111*a*-111*n* may also store content associated with the map platform 101, and/or the one or more services 113*a*-113*m*. In another embodiment, the one or more content providers 111*a*-111*n* may manage access to a central repository of data, and offer a consistent, standard interface to data.

By way of example, the user equipment (UE) 109 may be, or include, an embedded system, mobile terminal, fixed terminal, or portable terminal including a built-in navigation system, a personal navigation device, mobile handset, station, unit, device, multimedia computer, multimedia tablet, Internet node, communicator, desktop computer, laptop computer, notebook computer, netbook computer, tablet computer, personal communication system (PCS) device, personal digital assistants (PDAs), audio/video player, digital camera/camcorder, positioning device, fitness device, television receiver, radio broadcast receiver, electronic book device, game device, or any combination thereof, including the accessories and peripherals of these devices, or any combination thereof. It is also contemplated that the UE 109 may support any type of interface with a user (e.g., by way of various buttons, touch screens, consoles, displays, speakers, "wearable" circuitry, and other I/O elements or devices). Although shown in FIG. 1 as being separate from the vehicle 105, in some embodiments, the UE 109 may be integrated into, or part of, the vehicle 105.

In one embodiment, the UE 109, may execute one or more applications 117 (e.g., software applications) configured to carry out steps in accordance with methods described here. For instance, in one non-limiting example, the application 117 may carry out steps for determining a route for mood improvement. In another non-limiting example, application 117 may also be any type of application that is executable on the UE 109 and/or vehicle 105, such as autonomous driving applications, mapping applications, location-based service applications, navigation applications, content provisioning services, camera/imaging application, media player applications, social networking applications, calendar applications, and the like. In yet another non-limiting example, the application 117 may act as a client for the data analysis system 103 and perform one or more functions associated with determining a route for mood improvement, either alone or in combination with the data analysis system 103.

In some embodiments, the UE 109 and/or the vehicle 105 may include various sensors for acquiring a variety of different data or information. For instance, the UE 109, and/or the vehicle 105 may include one or more camera/imaging devices for capturing imagery (e.g., terrestrial images), global positioning system (GPS) sensors or Global Navigation Satellite System (GNSS) sensors for gathering location or coordinates data, network detection sensors for detecting wireless signals, receivers for carrying out different short-range communications (e.g., Bluetooth, Wi-Fi, Li-Fi, near field communication (NFC) etc.), temporal information sensors, Light Detection and Ranging (LIDAR) sensors, Radio Detection and Ranging (RADAR) sensors, audio recorders for gathering audio data, velocity sensors, switch sensors for determining whether one or more vehicle switches are engaged, and others.

The UE 109 and/or the vehicle 105 may also include one or more light sensors, height sensors, accelerometers (e.g., for determining acceleration and vehicle orientation), magnetometers, gyroscopes, inertial measurement units (IMUs), tilt sensors (e.g., for detecting the degree of incline or decline), moisture sensors, pressure sensors, and so forth. Further, the UE 109 and/or the vehicle 105 may also include sensors for detecting the relative distance of the vehicle 105 from a lane or roadway, the presence of other vehicles, pedestrians, traffic lights, lane markings, speed limits, road dividers, potholes, and any other objects, or a combination thereof. Other sensors may also be configured to detect weather data, traffic information, or a combination thereof. Yet other sensors may also be configured to determine the status of various control elements of the car, such as activation of wipers, use of a brake pedal, use of an acceleration pedal, angle of the steering wheel, activation of hazard lights, activation of head lights, and so forth.

In some embodiments, the UE 109 and/or the vehicle 105 may include GPS, GNSS or other satellite-based receivers configured to obtain geographic coordinates from a satellite 119 for determining current location and time. Further, the location can be determined by visual odometry, triangulation systems such as A-GPS, Cell of Origin, or other location extrapolation technologies, and so forth. In some embodiments, two or more sensors or receivers may be co-located with other sensors on the UE 109 and/or the vehicle 105.

By way of example, the map platform 101, the services platform 113, and/or the one or more content providers 111a-111n communicate with each other and other components of the system 100 using well known, new or still developing protocols. In this context, a protocol includes a set of rules defining how the network nodes within the communication network 115 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically affected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2:
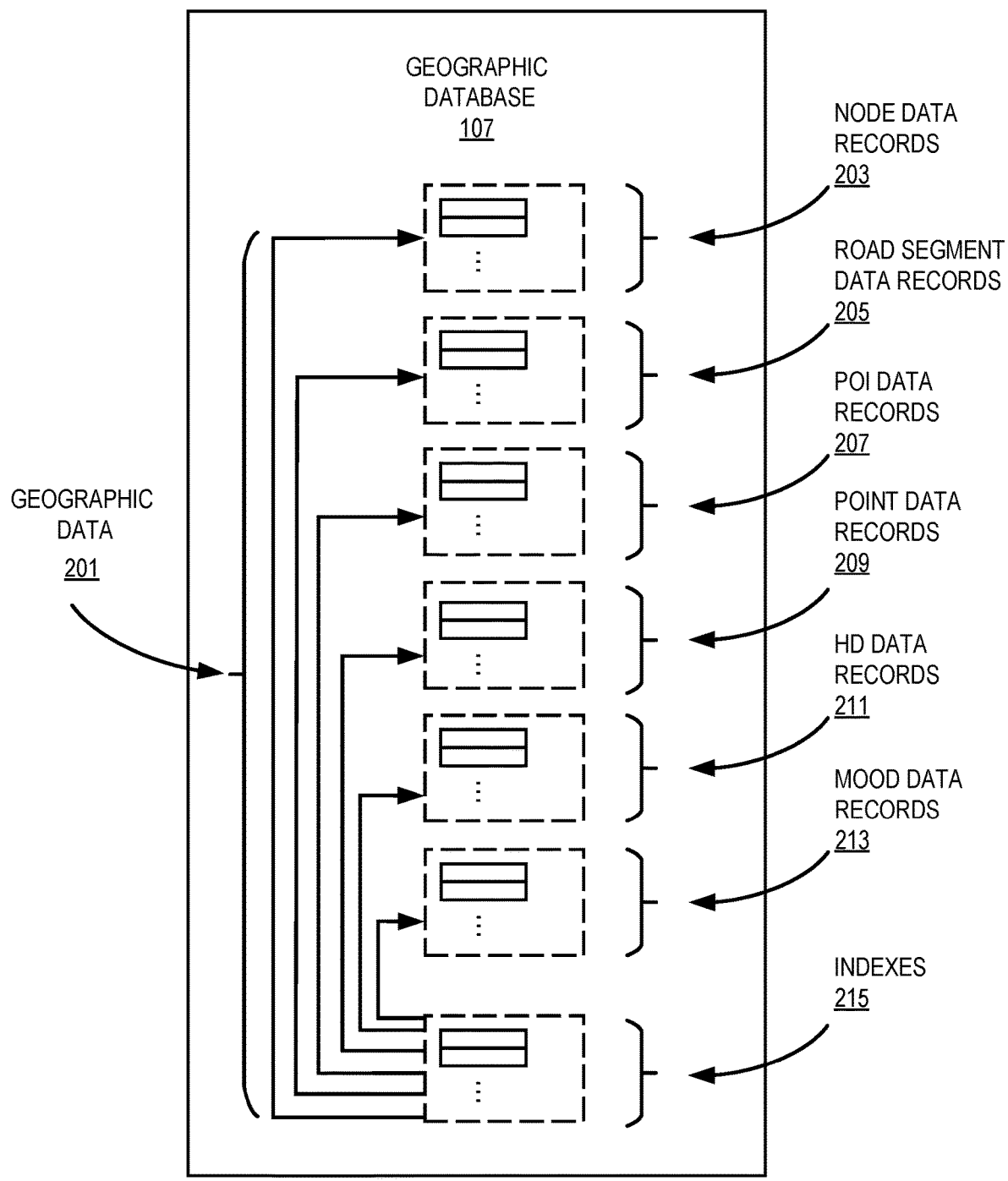
FIG. 2 is a diagram of a geographic database, in accordance with aspects of the present disclosure.

FIG. 2 is a diagram of the geographic database 107 of system 100, according to exemplary embodiments. In the exemplary embodiments, the information generated by the map platform 101 can be stored, associated with, and/or linked to the geographic database 107 or data thereof. In one embodiment, the geographic database 107 includes geographic data 201 used for (or configured to be compiled to be used for) mapping and/or navigation-related services, such as for personalized route determination, according to exemplary embodiments. For example, the geographic database 107 includes node data records 203, road segment data records 205, POI data records 207, point data records 209, HD data records 211, mood data records 213, and indexes 215, for example. More, fewer or different data records can be provided. In one embodiment, other data records include cartographic ("carto") data records, routing data, traffic data, weather data, and maneuver data. In one example, the other data records include data that is associated with certain POIs, roads, or geographic areas. In one example, the data is stored for utilization by a third-party. In one embodiment, the other data records include weather data records such as weather data reports. In one embodiment, the other data records include traffic data records such as traffic data reports. For example, the weather data records or the traffic data records can be associated with any of the map features stored in the geographic database 107 (e.g., a specific road or link, node, intersection, area, POI, etc.) on which the weather data or traffic data was collected. One or more portions, components, areas, layers, features, text, and/or symbols of the POI or event data can be stored in, linked to, and/or associated with one or more of these data records. For example, one or more portions of the POI, event data, or recorded route information can be matched with respective map or geographic records via position or GPS data associations (such as using the point-based map matching embodiments describes herein), for example.

In one embodiment, geographic features (e.g., two-dimensional or three-dimensional features) are represented using polygons (e.g., two-dimensional features) or polygon extrusions (e.g., three-dimensional features). For example, the edges of the polygons correspond to the boundaries or edges of the respective geographic feature. In the case of a building, a two-dimensional polygon can be used to represent a footprint of the building, and a three-dimensional polygon extrusion can be used to represent the three-dimensional surfaces of the building. It is contemplated that although various embodiments are discussed with respect to two-dimensional polygons, it is contemplated that the embodiments are also applicable to three-dimensional polygon extrusions, models, routes, etc. Accordingly, the terms polygons and polygon extrusions/models as used herein can be used interchangeably.

In one embodiment, the following terminology applies to the representation of geographic features in the geographic database 107.

"Node"—A point that terminates a link.

"Line segment"—A straight line connecting two points.

"Link" (or "edge")—A contiguous, non-branching string of one or more line segments terminating in a node at each end.

"Shape point"—A point along a link between two nodes (e.g., used to alter a shape of the link without defining new nodes).

"Oriented link"—A link that has a starting node (referred to as the "reference node") and an ending node (referred to as the "non reference node").

"Simple polygon"—An interior area of an outer boundary formed by a string of oriented links that begins and ends in one node. In one embodiment, a simple polygon does not cross itself "Polygon"—An area bounded by an outer boundary and none or at least one interior boundary (e.g., a hole or island). In one embodiment, a polygon is constructed from one outer simple polygon and none or at least one inner simple polygon. A polygon is simple if it just consists of one simple polygon, or complex if it has at least one inner simple polygon.

In one embodiment, the geographic database 107 follows certain conventions. For example, links do not cross themselves and do not cross each other except at a node or vertex. Also, there are no duplicated shape points, nodes, or links. Two links that connect each other have a common node or vertex. In the geographic database 107, overlapping geographic features are represented by overlapping polygons. When polygons overlap, the boundary of one polygon crosses the boundary of the other polygon. In the geographic database 107, the location at which the boundary of one polygon intersects they boundary of another polygon is represented by a node. In one embodiment, a node may be used to represent other locations along the boundary of a polygon than a location at which the boundary of the polygon intersects the boundary of another polygon. In one embodiment, a shape point is not used to represent a point at which the boundary of a polygon intersects the boundary of another polygon.

In one embodiment, the geographic database 107 is presented according to a hierarchical or multi-level tile projection. More specifically, in one embodiment, the geographic database 107 may be defined according to a normalized Mercator projection. Other projections may be used. In one embodiment, a map tile grid of a Mercator or similar projection can a multilevel grid. Each cell or tile in a level of the map tile grid is divisible into the same number of tiles of that same level of grid. In other words, the initial level of the map tile grid (e.g., a level at the lowest zoom level) is divisible into four cells or rectangles. Each of those cells are in turn divisible into four cells, and so on until the highest zoom level of the projection is reached.

In one embodiment, the map tile grid may be numbered in a systematic fashion to define a tile identifier (tile ID). For example, the top left tile may be numbered 00, the top right tile may be numbered 01, the bottom left tile may be numbered 10, and the bottom right tile may be numbered 11. In one embodiment, each cell is divided into four rectangles and numbered by concatenating the parent tile ID and the new tile position. A variety of numbering schemes also is possible. Any number of levels with increasingly smaller geographic areas may represent the map tile grid. Any level (n) of the map tile grid has $2(n+1)$ cells. Accordingly, any tile of the level (n) has a geographic area of $A/2(n+1)$ where A is the total geographic area of the world or the total area of the map tile grids. Because of the numbering system, the exact position of any tile in any level of the map tile grid or projection may be uniquely determined from the tile ID.

In one embodiment, the system 100 may identify a tile by a quadkey determined based on the tile ID of a tile of the map tile grid. The quadkey, for example, is a one dimensional array including numerical values. In one embodiment, the quadkey may be calculated or determined by interleaving the bits of the row and column coordinates of a tile in the grid at a specific level. The interleaved bits may be converted to a predetermined base number (e.g., base 10, base 4, hexadecimal). In one example, leading zeroes are inserted or retained regardless of the level of the map tile grid in order to maintain a constant length for the one-dimensional array of the quadkey. In another example, the length of the one-dimensional array of the quadkey may indicate the corresponding level within the map tile grid. In one embodiment, the quadkey is an example of the hash or encoding scheme of the respective geographical coordinates of a geographical data point that can be used to identify a tile in which the geographical data point is located.

In exemplary embodiments, the road segment data records 205 are links or segments representing roads, streets, or paths, as can be used in the calculated route or recorded route information for determination of one or more personalized routes, according to exemplary embodiments. The node data records 203 are end points or vertices (such as intersections) corresponding to the respective links or segments of the road segment data records 205. The road segment data records 205 and the node data records 203 represent a road network, such as used by vehicles, cars, and/or other entities. Alternatively, the geographic database 107 can contain path segment and node data records or other data that represent pedestrian paths or areas in addition to or instead of the vehicle road record data, for example. In one embodiment, the road or path segments can include an altitude component to extend to paths or road into three-dimensional space (e.g., to cover changes in altitude and contours of different map features, and/or to cover paths traversing a three-dimensional airspace).

The road/link segments and nodes can be associated with attributes, such as geographic coordinates, street names, address ranges, speed limits, turn restrictions at intersections, and other navigation related attributes, as well as POIs, such as gasoline stations, hotels, restaurants, museums, stadiums, offices, automobile dealerships, auto repair shops, buildings, stores, parks, etc. The geographic database 107 can include data about the POIs and their respective locations in the POI data records 207. In one example, the POI data records 207 may include the hours of operation for various businesses. The geographic database 107 can also include data about places, such as cities, towns, or other communities, and other geographic features, such as bodies of water, mountain ranges, etc. Such place or feature data can be part of the POI data records 207 or can be associated with POIs or POI data records 207 (such as a data point used for displaying or representing a position of a city).

As shown in FIG. 2, the geographic database 107 may also include point data records 209 for storing the point data, map features, as well as other related data used according to the various embodiments described herein. In addition, the point data records 209 can also store ground truth training and evaluation data, machine learning models, annotated observations, and/or any other data. By way of example, the point data records 209 can be associated with one or more of the node data records 203, road segment data records 205, and/or POI data records 207 to support verification, localization or visual odometry based on the features stored therein and the corresponding estimated quality of the features. In this way, the point data records 209 can also be associated with or used to classify the characteristics or metadata of the corresponding records 203, 205, and/or 207.

As discussed above, the HD data records 211 may include models of road surfaces and other map features to centimeter-level or better accuracy. The HD data records 211 may also include models that provide the precise lane geometry with lane boundaries, as well as rich attributes of the lane models. These rich attributes may include, but are not limited to, lane traversal information, lane types, lane marking types, lane level speed limit information, and/or the like. In one embodiment, the HD data records 211 may be divided into spatial partitions of varying sizes to provide HD mapping data to vehicles and other end user devices with near real-time speed without overloading the available resources of these vehicles and devices (e.g., computational, memory, bandwidth, etc. resources). In some implementations, the HD data records 211 may be created from high-resolution 3D mesh or point-cloud data generated, for instance, from LiDAR-equipped vehicles. The 3D mesh or point-cloud data may be processed to create 3D representations of a street or geographic environment at centimeter-level accuracy for storage in the HD data records 211.

In one embodiment, the HD data records 211 also include real-time sensor data collected from probe vehicles in the field. The real-time sensor data, for instance, integrates real-time traffic information, weather, and road conditions (e.g., potholes, road friction, road wear, etc.) with highly detailed 3D representations of street and geographic features to provide precise real-time also at centimeter-level accuracy. Other sensor data can include vehicle telemetry or operational data such as windshield wiper activation state, braking state, steering angle, accelerator position, and/or the like.

In one embodiment, the mood data records 213 include sensor data, location data, vehicle data, and mood data. In one example, the sensor data may include the types of sensors used to capture the sensor data associated with an individual's mood. In one example, the location data may be determined according to one or more GPS sensors. In another example, the location data may include data determined by an analysis of mobility patterns. In one example, the vehicle data may include one or more aspects (e.g., vehicle sensors, cabin features, autonomous driving capabilities, etc.) associated with one or more vehicles for transporting an individual. In one example, the mood data include mood improvement data that is associated with certain POIs, roads, or geographic areas. In one example, the mood data records 213 are stored for utilization by a third-party. One or more portions, components, areas, layers, features, text, and/or symbols of the POI or event data can be stored in, linked to, and/or associated with one or more of these data records. For example, one or more portions of the POI, event data, or recorded route information can be matched with respective map or geographic records via position or GPS data associations (such as using the point-based map matching embodiments describes herein), for example.

The indexes 215 in FIG. 2 may be used improve the speed of data retrieval operations in the geographic database 107. Specifically, the indexes 215 may be used to quickly locate data without having to search every row in the geographic database 107 every time it is accessed. For example, in one embodiment, the indexes 215 can be a spatial index of the polygon points associated with stored feature polygons.

The geographic database 107 can be maintained by the one or more content providers 111a-111n in association with the services platform 113 (e.g., a map developer). The map developer can collect geographic data to generate and enhance the geographic database 107. There can be different ways used by the map developer to collect data. These ways can include obtaining data from other sources, such as municipalities or respective geographic authorities. In addition, the map developer can employ field personnel to travel by vehicle along roads throughout the geographic region to observe features and/or record information about them, for example. Also, remote sensing, such as aerial or satellite photography, can be used.

The geographic database 107 can be a master geographic database stored in a format that facilitates updating, maintenance, and development. For example, the master geographic database 107 or data in the master geographic database 107 can be in an Oracle spatial format or other spatial format (for example, accommodating different map layers), such as for development or production purposes. The Oracle spatial format or development/production database can be compiled into a delivery format, such as a geographic data files (GDF) format. The data in the production and/or delivery formats can be compiled or further compiled to form geographic database products or databases, which can be used in end user navigation devices or systems.

For example, geographic data is compiled (such as into a platform specification format (PSF) format) to organize and/or configure the data for performing navigation-related functions and/or services, such as route calculation, route guidance, map display, speed calculation, distance and travel time functions, and other functions, by a navigation device. The navigation-related functions can correspond to vehicle navigation, pedestrian navigation, or other types of navigation. The compilation to produce the end user databases can be performed by a party or entity separate from the map developer. For example, a customer of the map developer, such as a navigation device developer or other end user device developer, can perform compilation on a received geographic database in a delivery format to produce one or more compiled navigation databases.

Figure 3:
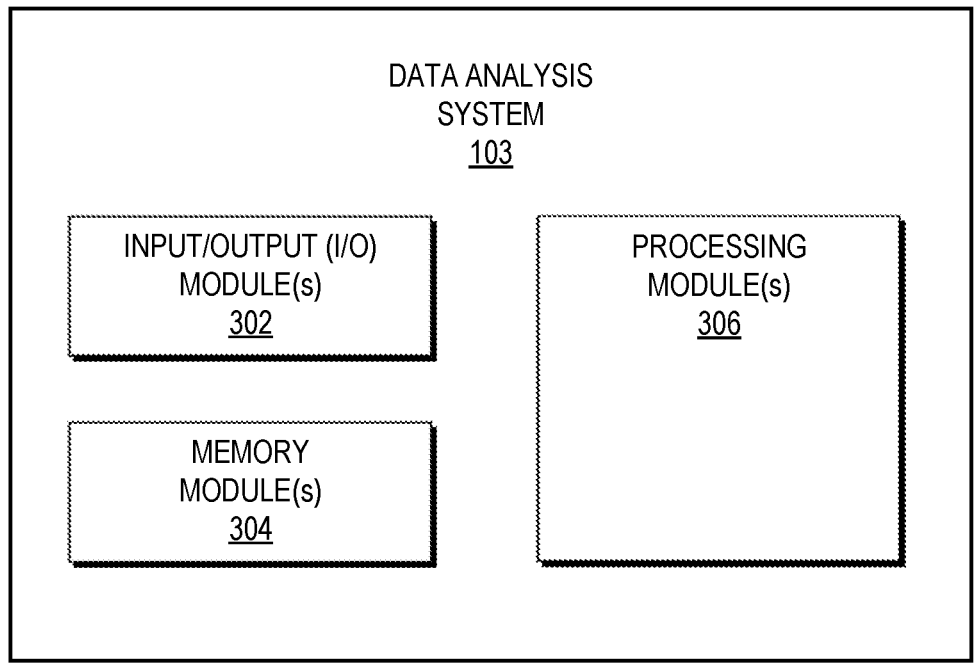
FIG. 3 is a diagram of the components of a data analysis system, in accordance with aspects of the present disclosure.

FIG. 3 is a diagram of the components of the data analysis system 103 of FIG. 1, according to one embodiment. By way of example, the data analysis system 103 includes one or more components for determining a route for mood improvement according to the various embodiments described herein. It is contemplated that the functions of these components may be combined or performed by other components of equivalent functionality. In this embodiment, data analysis system 103 includes in input/output module 302, a memory module 304, and a processing module 306. The above presented modules and components of the data analysis system 103 can be implemented in hardware, firmware, software, or a combination thereof. Though depicted as a separate entity in FIG. 1, it is contemplated that the data analysis system 103 may be implemented as a module of any of the components of the system 100 (e.g., a component of the services platform 113, etc.). In another embodiment, one or more of the modules 302-306 may be implemented as a cloud-based service, local service, native application, or combination thereof. The functions of these modules are discussed with respect to FIG. 4 below.

Figure 4:
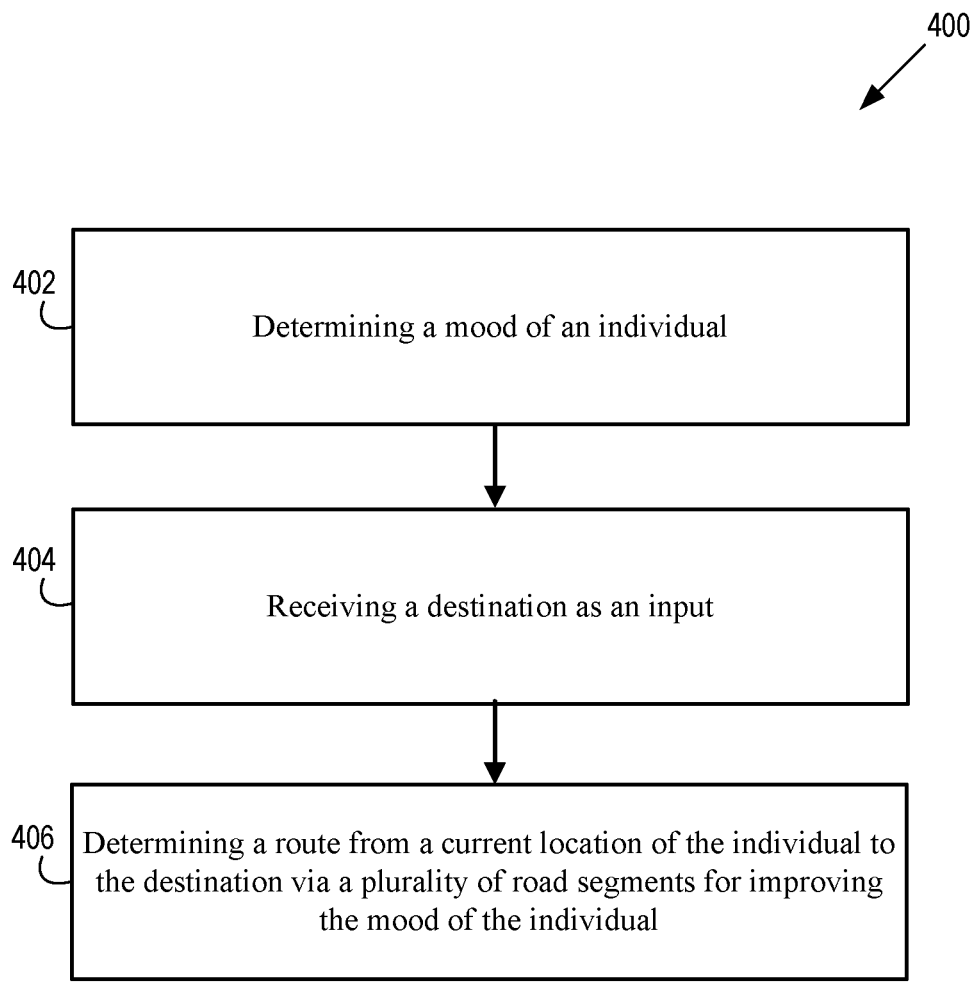
FIG. 4 is a flowchart setting forth steps of an example process, in accordance with aspects of the present disclosure.

FIG. 4 is a flowchart of an example method, in accordance with at least some of the embodiments described herein. Although the blocks in FIG. 4 are illustrated in a sequential order, the blocks may in some instances be performed in parallel, and/or in a different order than those described therein. Also, the various blocks may be combined into fewer blocks, divided into additional blocks, and/or removed based upon the desired implementation.

In addition, the flowchart of FIG. 4 shows the functionality and operation of one possible implementation of the present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer-readable media that stores data for short periods of time, such as register memory, processor cache, or Random Access Memory (RAM), and/or persistent long term storage, such as read only memory (ROM), optical or magnetic disks, or compact-disc read only memory (CD-ROM), for example. The computer readable media may also be, or include, any other volatile or non-volatile storage systems. The computer readable medium may be considered a computer readable storage medium, a tangible storage device, or other article of manufacture, for example.

Alternatively, each block in FIG. 4 may represent circuitry that is wired to perform the specific logical functions in the process. Illustrative methods, such as the method shown in FIG. 4, may be carried out in whole or in part by a component or components in the cloud and/or system. However, it should be understood that the example method may instead be carried out by other entities or combinations of entities (i.e., by other computing devices and/or combinations of computing devices), without departing from the scope of the invention. For example, functions of the method of FIG. 4, may be fully performed by a computing device (or components of a computing device such as one or more processors), or may be distributed across multiple components of the computing device, across multiple computing devices, and/or across a server.

Referring to FIG. 4, an example method 400 may include one or more operations, functions, or actions as illustrated by blocks 402-406. The blocks 402-406 may be repeated periodically or performed intermittently, or as prompted by a user, device or system. In one embodiment, the method 400 is implemented in whole or in part by the data analysis system 103 of FIG. 3.

As shown by block 402, the method 400 includes determining a mood of an individual. In one example, the processing module 306 of FIG. 3 is configured to determine a mood of an individual. In one example, the input/output module 302 of FIG. 3 is configured to receive sensor data from one or more sensors associated with the system 100 of FIG. 1. In this example, the input/output module 306 is configured to provide the sensor data to the processing module 306 for determining the mood of the individual. In one example, the mood is determined without the individual needing to enter any information manually. In another example, the mood of the individual is entered by the individual via an electronic device. In one example, the mood of the individual may be a numerical score in a range (e.g., 1-5, etc.). In another example, the mood of the individual may be a binary score (e.g., "Satisfactory" or "Unsatisfactory", etc.) that is associated with one or more thresholds corresponding to one or more metrics (e.g., heart rate, sleep, movement, caloric expenditure, temperature, etc.). In one example, the binary score may also be represented and displayed as a pair of images (e.g., a thumbs up and a thumbs down).

In one example, the mood is based on one or more measurements of the individual during one or more predetermined periods of time. For example, the amount of time the individual was sleeping during a night may be analyzed in addition to the amount of movement the individual has performed during the following day. Continuing with this example, based on an analysis of those two metrics the processing module 306 of FIG. 3 may determine the mood of the individual. In one scenario, sensor data captured by wearable electronic devices and other sensors may indicate that the individual slept less than 5 hours during the night and walked over 20,000 steps the following day. In this scenario, based on the metrics corresponding to sleep and movement the processing module 306 may be configured to determine that the mood of the individual is unsatisfactory. In another scenario, sensor data captured by wearable electronic devices and other sensors may indicate that the individual slept at least 7 hours of sleep during the night and walked less than 10,000 steps during the following day. In this scenario, the processing module 306 may be configured to determine that the mood of the individual is satisfactory.

In one example, determining the mood of the individual is based on an analysis of a mobility pattern of the individual. Information of an individual's location history or insights related to an individual's mobility patterns (e.g., mobility data) can be found via, for instance, location data (e.g., Global Positioning System (GPS) or equivalent data) recorded by a user device and/or a vehicle, other sensor data from user devices and/or vehicles, IP addresses of Wi-Fi access points, cell towers, and/or Bluetooth-enabled devices of other users and/or entities, private, public, and/or national surveillance systems (e.g., via cameras, satellites, internet, etc.), social media location check-in data, etc.

In one embodiment, the system 100 of FIG. 1 retrieves individual historical mobility data from individual device sensor data, vehicle data (e.g., individual historical mobility data and/or real-time information), etc., and builds an individual mobility pattern model. In one instance, the system 100 can gather all individual mobility data in order to generate the individual mobility pattern model. By way of example, the insights may include when and where the individual travels to a location, and the used mode(s) of transport (i.e., checked-out); when and where each mode of transport is released (i.e., checked-in); how long the individual stays at a given location; where the individual is located within the threshold proximity to a point of interest (e.g., restaurant, supermarket, park, etc.) at a given time; correlations that can be made relative to other factors such as weather, events, day of the week, etc.

In one example, the mobility pattern includes an individual mobility pattern, a vehicle mobility pattern, or a combination thereof under one or more contexts for travel to or from a plurality of locations. In another example, the processing module 306 of FIG. 3 is configured to analyze the mobility patterns with respect to a vehicle type (e.g., a bus, a car, a bicycle, a scooter), a vehicle operator (e.g., Company A, Company B, Company C, etc.), or a combination thereof. In one example, the mobility patterns may be based on historical mobility data or real-time mobility data.

In another example, the processing module 306 of FIG. 3 is configured to determine the mood of the individual is based on one or more metrics of the individual captured via one or more sensors. In one example, the one or more metrics captured via the one or more sensors may include measurements that correspond to the heart rate, sleep, movement, caloric expenditure, temperature of an individual. In one example, each of the measurements that correspond to the heart rate, sleep, movement, caloric expenditure, temperature of the individual may be associated with various thresholds that are specific to the individual. For example, a first individual may be associated with a resting heart rate threshold of 70 beats per minutes (bpm) while a second individual may be associated with a resting heart rate threshold of 80 bpm. In this example, based on the data detected by one or more sensors, if it is detected that the first individual's heart rate was over 80 bpm for a prolonged period of time, then the mood of the first individual may be determined to be within a lower range based on the resting heart threshold of 70 bpm. Continuing with this example, based on the data detected by one or more sensors, however, if it is detected that the second individual's heart rate was over 80 bpm for a prolonged period of time, then the mood of the second individual may be determined to be within an expected range based on the resting heart rate threshold of 80 bpm.

As shown by block 404, the method 400 also includes receiving a destination as an input. In one example, the processing module 306 of FIG. 3 is configured to receive a destination, via the input/output module 302 of FIG. 3, as an input. In one embodiment, an individual may enter the destination via an electronic device (e.g., User Equipment 109 of FIG. 1).

As shown by block 406, the method 400 also includes determining a route from a current location of the individual to the destination via a plurality of road segments for improving the mood of the individual. In one example, the processing module 306 of FIG. 3 is configured to determine a route from a current location of the individual to the destination via a plurality of road segments for improving the mood of the individual. In one example, identification of one or more road segments of the plurality of road segments to be part of the route is based on mood data associated with the one or more road segments. In one example, the mood data associated with the one or more road segments is based on one or more visual aspects associated with the one or more road segments. For example, the mood data associated with the one or more road segments may be based on one or more points of interest that are viewable while the individual is traveling in a given vehicle. In one scenario, the mood data of a road segment that allows an individual to view a natural landscape (e.g., a body of water, mountains, forests, etc.) may be associate with a higher probability of improving the mood of an individual than a road segment that allows an individual to view an industrial setting (e.g., factories, warehouses, etc.).

In one example, the mood data includes temporal elements corresponding to the one or more road segments of the plurality of the road segments. For example, the mood data associated with a road segment that is nearby a body of water may include temporal elements that specify the amount of potential improvement in the mood of an individual during specific time periods. In one scenario, traveling along a particular road segment that is nearby a body of water during the day may have a greater likelihood of improving the mood of an individual as opposed to traveling along that particular road segment during the night. In this scenario, depending on the time that is associated with the request for transporting an individual from a current location to a destination, the processing module 306 of FIG. 3 may select one or more road segments based on one or more associated temporal elements.

In one embodiment, the method 400 may further include determining one or more elements of travel for improving the mood of the individual. In one example, the processing module 306 of FIG. 3 is configured to determine one or more elements of travel for improving the mood of the individual. For example, the one or more elements of travel may include the static and dynamic attributes of one or more road segments that form a route from the current location of the individual to the destination. In one example, the processing module 306 may be configured to analyze static attributes such as the associated levels of autonomous driving needed to travel along one or more of the road segments that form the route. In this example, the processing module 306 may be configured to select one or more road segments that form the route based on static attributes that will contributed to a smoother ride for the individual. In another example, the processing module 306 may be configured to analyze dynamic attributes such as weather data and traffic data along the one or more of the road segments that form the route. In this example, the processing module 306 may be configured to select one or more road segments that form the route based on minimizing unfavorable weather or heaver traffic along one or more road segments in order to provide a more enjoyable experience for the individual.

In another embodiment, the method 400 may further include, based on the determined route, determining an autonomous vehicle for transporting the individual. In one example, the processing module 306 of FIG. 3 is configured to, based on the determined route, determine an autonomous vehicle for transporting the individual. In one scenario, the determined route may be associated with heavier traffic than usual while transporting the individual. In this scenario, the processing module 306 may be configured to select an autonomous vehicle that comprises a large cabin (e.g., a cabin in a sports utility vehicle) in order to optimize the chances of improving the mood of the individual as the individual waits in traffic. In another scenario, the determined route may be associated with inclement weather along the route for transporting the individual. In this scenario, the processing module 306 may be configured to select an autonomous vehicle that is equipped with additional sensors for traveling in inclement weather. Continuing with this scenario, an autonomous vehicle that is equipped with additional sensors for traveling in inclement weather may not require the individual to assume control of the vehicle and thereby optimize the chances of improving the mood of the individual as the individual travels to a destination during a severe storm.

In one embodiment, the method 400 may further include determining autonomous vehicle level data associated with one or more aspects of the determined route for transporting the individual. In one example, the processing module 306 of FIG. 3 is configured to determine autonomous vehicle level data associated with one or more aspects of a route for transporting the individual. In one example, the processing module 306 may be configured to analyze the autonomous vehicle level data when comparing one or more autonomous vehicles that are available for transporting the individual from a current location to a destination. Continuing with this example, based on the analysis, the processing module 306 may be configured to select an autonomous vehicle from one or more autonomous vehicles that is best equipped to transport the individual by minimizing the amount of time that an individual may need to assume control of the vehicle during the route.

In another embodiment, the method 400 may further include analyzing one or more attributes of one or more autonomous vehicles. In this embodiment, the method 400 may further include, based on the determined route and the analysis of the one or more attributes of the one or more autonomous vehicles, selecting an autonomous vehicle from the one or more autonomous vehicles. In one example, the processing module 306 of FIG. 3 is configured to analyze one or more attributes of one or more autonomous vehicles. Continuing with this example, the processing module 306 is configured to, based on the determined route and the analysis of the one or more attributes of the one or more autonomous vehicles, select an autonomous vehicle from the one or more autonomous vehicles. In one scenario, the processing module 306 may be configured to select an autonomous vehicle that is a convertible based on favorable weather conditions along the route selected to transport the individual. In another scenario, the processing module 306 may be configured to select an autonomous vehicle that is equipped with specific entertainment options based on unfavorable traffic conditions along the route selected to transport the individual.

The processes described herein for determining a route for mood improvement may be advantageously implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 5:
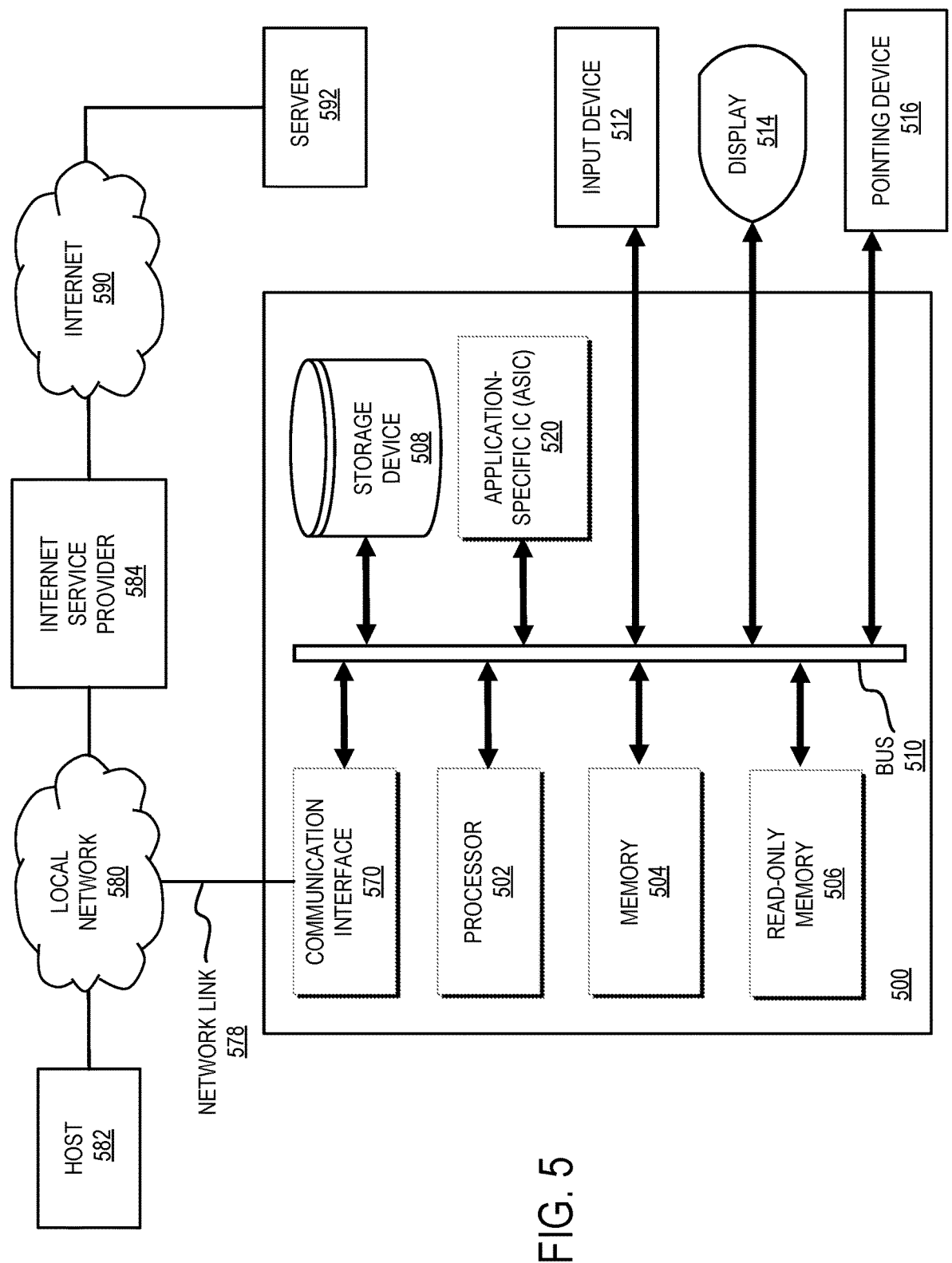
FIG. 5 is a diagram of an example computer system, in accordance with aspects of the present disclosure.

FIG. 5 illustrates a computer system 500 upon which an embodiment may be implemented. Computer system 500 is programmed (e.g., via computer program code or instructions) to provide information for determining a route for mood improvement as described herein and includes a communication mechanism such as a bus 510 for passing information between other internal and external components of the computer system 500. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range.

A bus 510 includes one or more parallel conductors of information so that information is transferred quickly among devices coupled to the bus 510. One or more processors 502 for processing information are coupled with the bus 510.

A processor 502 performs a set of operations on information as specified by computer program code related to determining a route for mood improvement. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 510 and placing information on the bus 510. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 502, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 500 also includes a memory 504 coupled to bus 510. The memory 504, such as a random access memory (RAM) or other dynamic storage device, stores information including processor instructions for determining a route for mood improvement. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of processor instructions. The computer system 700 also includes a read only memory (ROM) 506 or other static storage device coupled to the bus 510 for storing static information, including instructions, that is not changed by the computer system 500. Some memory is composed of volatile storage that loses the information stored thereon when power is lost. Also coupled to bus 510 is a non-volatile (persistent) storage device 508, such as a magnetic disk, optical disk or flash card, for storing information, including instructions, that persists even when the computer system 500 is turned off or otherwise loses power.

Information, including instructions for determining a route for mood improvement, is provided to the bus 510 for use by the processor from an external input device 512, such as a keyboard containing alphanumeric keys operated by a human user, or a sensor. A sensor detects conditions in its vicinity and transforms those detections into physical expression compatible with the measurable phenomenon used to represent information in computer system 500. Other external devices coupled to bus 510, used primarily for interacting with humans, include a display 514, such as a cathode ray tube (CRT) or a liquid crystal display (LCD), or plasma screen or printer for presenting text or images, and a pointing device 516, such as a mouse or a trackball or cursor direction keys, or motion sensor, for controlling a position of a small cursor image presented on the display 514 and issuing commands associated with graphical elements presented on the display 514. In some embodiments, for example, in embodiments in which the computer system 500 performs all functions automatically without human input, one or more of external input device 512, display device 514 and pointing device 516 is omitted.

In the illustrated embodiment, special purpose hardware, such as an application specific integrated circuit (ASIC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

The computer system 500 may also include one or more instances of a communications interface 570 coupled to bus 510. The communication interface 570 may provide a one-way or two-way communication coupling to a variety of external devices that operate with their own processors, such as printers, scanners and external disks. In addition, the communication interface 570 may provide a coupling to a local network 580, by way of a network link 578. The local network 580 may provide access to a variety of external devices and systems, each having their own processors and other hardware. For example, the local network 580 may provide access to a host 582, or an internet service provider 584, or both, as shown in FIG. 5. The internet service provider 584 may then provide access to the Internet 590, in communication with various other servers 592.

Computer system 500 also includes one or more instances of a communication interface 570 coupled to bus 510. Communication interface 570 provides a one-way or two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, the communication interface 570 is an integrated services digital network (ISDN) card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, the communication interface 570 may be a local area network (LAN) card to provide a data communication connection to a compatible LAN, such as Ethernet. Wireless links may also be implemented. For wireless links, the communication interface 570 sends or receives or both sends and receives electrical, acoustic or electromagnetic signals, including infrared and optical signals, that carry information streams, such as digital data. For example, in wireless handheld devices, such as mobile telephones like cell phones, the communication interface 570 includes a radio band electromagnetic transmitter and receiver called a radio transceiver. In certain embodiments, the communication interface 570 enables connection to the communication network 115 of FIG. 1 for providing information for determining a route for mood improvement.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read.

Figure 6:
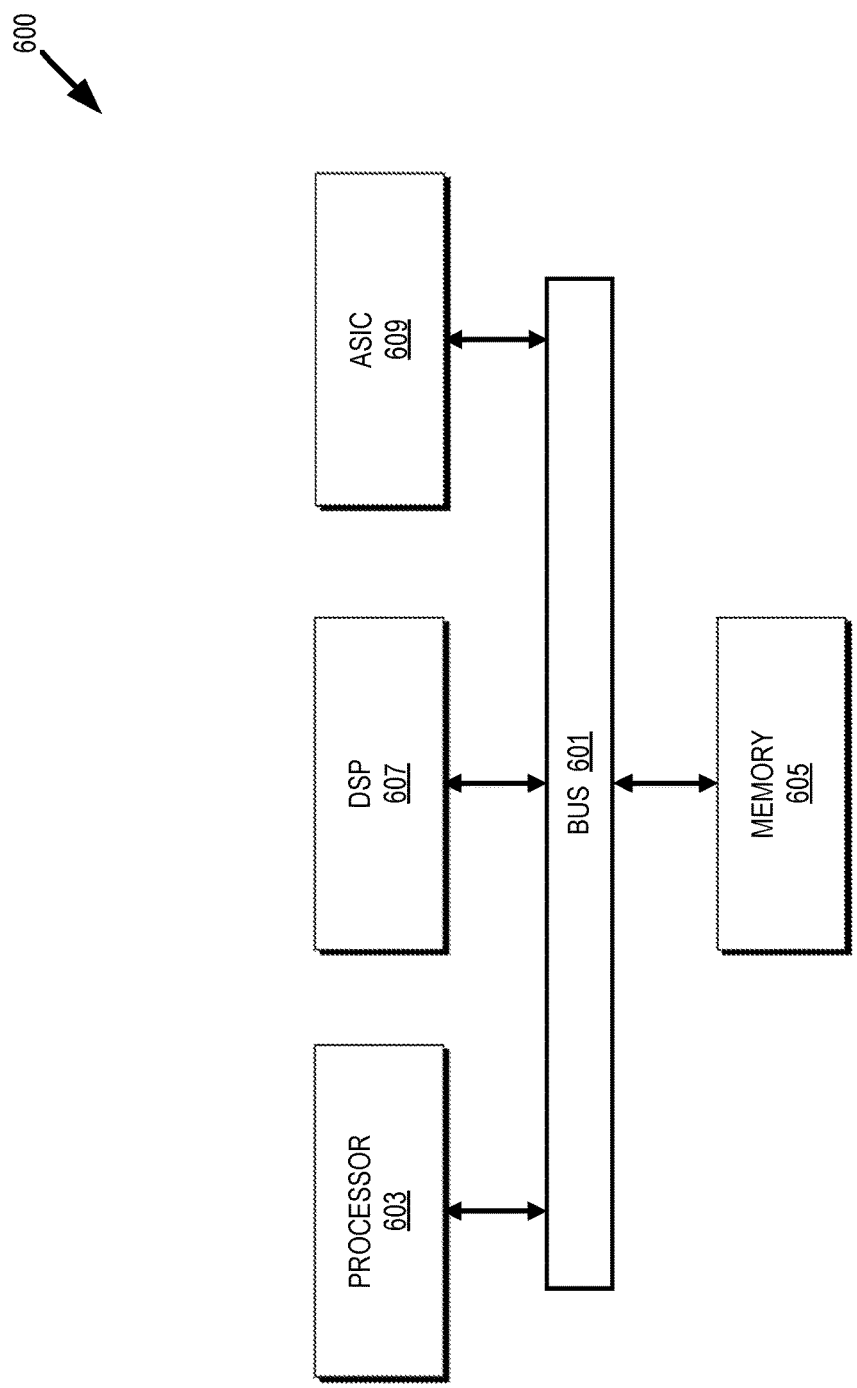
FIG. 6 is a diagram of an example chip set, in accordance with aspects of the present disclosure.

FIG. 6 illustrates a chip set 600 upon which an embodiment may be implemented. Chip set 600 is programmed to determine a route for mood improvement as described herein and includes, for instance, the processor and memory components described with respect to FIG. 6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip.

In one embodiment, the chip set 600 includes a communication mechanism such as a bus 601 for passing information among the components of the chip set 600. A processor 603 has connectivity to the bus 601 to execute instructions and process information stored in, for example, a memory 605. The processor 603 may include one or more processing cores with each core configured to perform independently. A multi-core processor enables multiprocessing within a single physical package. Examples of a multi-core processor include two, four, eight, or greater numbers of processing cores. Alternatively or in addition, the processor 603 may include one or more microprocessors configured in tandem via the bus 601 to enable independent execution of instructions, pipelining, and multithreading. The processor 603 may also be accompanied with one or more specialized components to perform certain processing functions and tasks such as one or more digital signal processors (DSP) 607, or one or more application-specific integrated circuits (ASIC) 609. A DSP 607 typically is configured to process real-world signals (e.g., sound) in real time independently of the processor 603. Similarly, an ASIC 609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 603 and accompanying components have connectivity to the memory 605 via the bus 601. The memory 605 includes both dynamic memory (e.g., RAM, magnetic disk, writable optical disk, etc.) and static memory (e.g., ROM, CD-ROM, etc.) for storing executable instructions that when executed perform the steps described herein to provide information for determining a route for mood improvement. The memory 605 also stores the data associated with or generated by the execution of the inventive steps.

Figure 7:
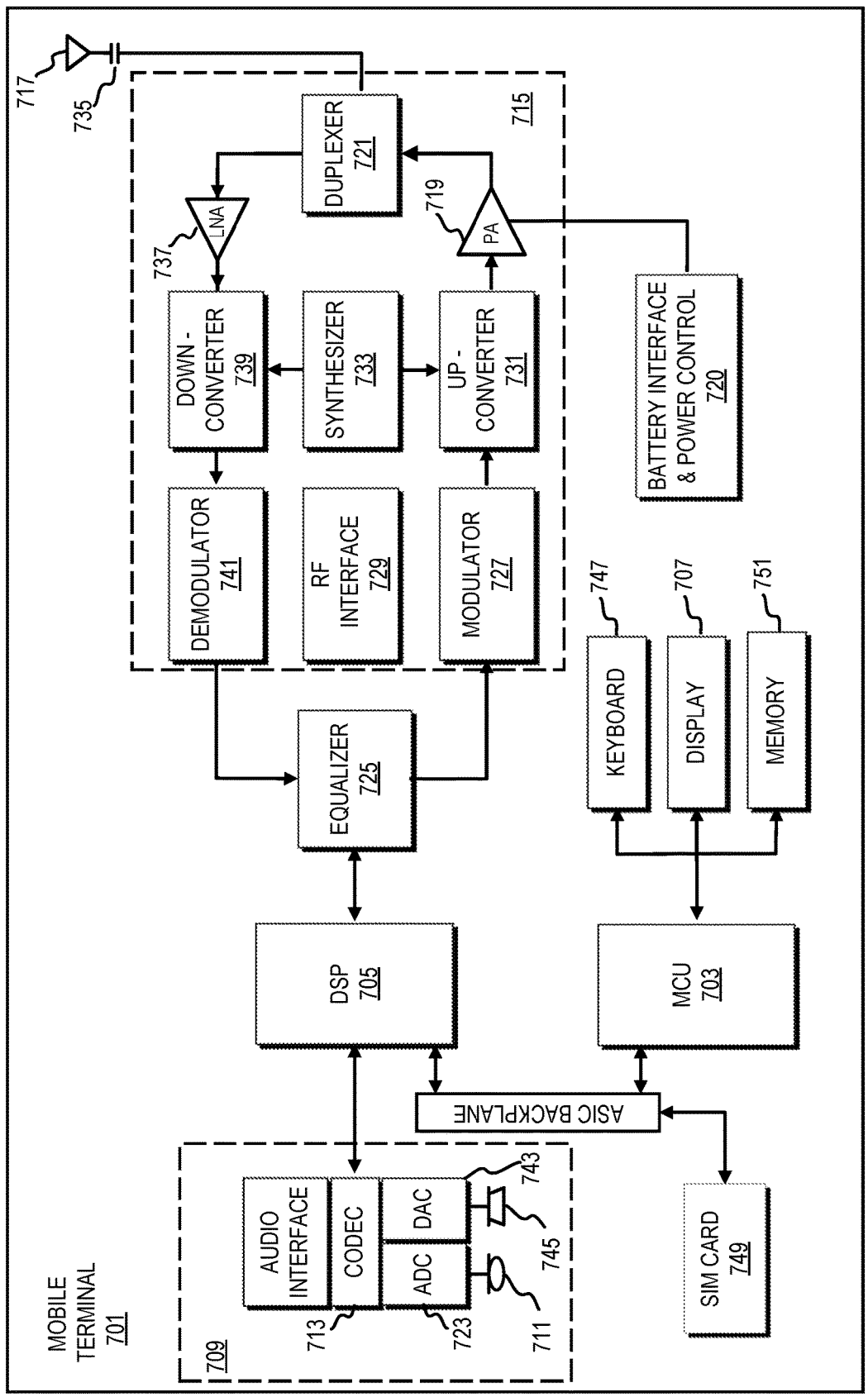
FIG. 7 is a diagram of an example mobile device, in accordance with aspects of the present disclosure.

FIG. 7 is a diagram of exemplary components of a mobile terminal 701 (e.g., a mobile device, vehicle, and/or part thereof) capable of operating in the system of FIG. 1, according to one embodiment. Generally, a radio receiver is often defined in terms of front-end and back-end characteristics. The front-end of the receiver encompasses all of the Radio Frequency (RF) circuitry whereas the back-end encompasses all of the base-band processing circuitry. Pertinent internal components of the telephone include a Main Control Unit (MCU) 703, a Digital Signal Processor (DSP) 705, and a receiver/transmitter unit including a microphone gain control unit and a speaker gain control unit. A main display unit 707 provides a display to the user in support of various applications and mobile station functions that offer automatic contact matching. An audio function circuitry 709 includes a microphone 711 and microphone amplifier that amplifies the speech signal output from the microphone 711. The amplified speech signal output from the microphone 711 is fed to a coder/decoder (CODEC) 713.

A radio section 715 amplifies power and converts frequency in order to communicate with a base station, which is included in a mobile communication system, via antenna 717. The power amplifier (PA) 719 and the transmitter/modulation circuitry are operationally responsive to the MCU 703, with an output from the PA 719 coupled to the duplexer 721 or circulator or antenna switch, as known in the art. The PA 719 also couples to a battery interface and power control unit 720.

In use, a user of mobile terminal 701 speaks into the microphone 711 and his or her voice along with any detected background noise is converted into an analog voltage. The analog voltage is then converted into a digital signal through the Analog to Digital Converter (ADC) 723. The control unit 703 routes the digital signal into the DSP 705 for processing therein, such as speech encoding, channel encoding, encrypting, and interleaving. In one embodiment, the processed voice signals are encoded, by units not separately shown, using a cellular transmission protocol such as global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, 5G networks, code division multiple access (CDMA), wireless fidelity (WiFi), satellite, and the like.

The encoded signals are then routed to an equalizer 725 for compensation of any frequency-dependent impairments that occur during transmission though the air such as phase and amplitude distortion. After equalizing the bit stream, the modulator 727 combines the signal with a RF signal generated in the RF interface 729. The modulator 727 generates a sine wave by way of frequency or phase modulation. In order to prepare the signal for transmission, an up-converter 731 combines the sine wave output from the modulator 727 with another sine wave generated by a synthesizer 733 to achieve the desired frequency of transmission. The signal is then sent through a PA 719 to increase the signal to an appropriate power level. In practical systems, the PA 719 acts as a variable gain amplifier whose gain is controlled by the DSP 705 from information received from a network base station. The signal is then filtered within the duplexer 721 and optionally sent to an antenna coupler 735 to match impedances to provide maximum power transfer. Finally, the signal is transmitted via antenna 717 to a local base station. An automatic gain control (AGC) can be supplied to control the gain of the final stages of the receiver. The signals may be forwarded from there to a remote telephone which may be another cellular telephone, other mobile phone or a land-line connected to a Public Switched Telephone Network (PSTN), or other telephony networks.

Voice signals transmitted to the mobile terminal 701 are received via antenna 717 and immediately amplified by a low noise amplifier (LNA) 737. A down-converter 739 lowers the carrier frequency while the demodulator 741 strips away the RF leaving only a digital bit stream. The signal then goes through the equalizer 725 and is processed by the DSP 705. A Digital to Analog Converter (DAC) 743 converts the signal and the resulting output is transmitted to the user through the speaker 745, all under control of a Main Control Unit (MCU) 703—which can be implemented as a Central Processing Unit (CPU) (not shown).

The MCU 703 receives various signals including input signals from the keyboard 747. The keyboard 747 and/or the MCU 703 in combination with other user input components (e.g., the microphone 711) comprise a user interface circuitry for managing user input. The MCU 703 runs a user interface software to facilitate user control of at least some functions of the mobile station 701 to provide information for determining a route for mood improvement. The MCU 703 also delivers a display command and a switch command to the display 707 and to the speech output switching controller, respectively. Further, the MCU 703 exchanges information with the DSP 705 and can access an optionally incorporated SIM card 749 and a memory 751. In addition, the MCU 703 executes various control functions required of the station. The DSP 705 may, depending upon the implementation, perform any of a variety of conventional digital processing functions on the voice signals. Additionally, DSP 705 determines the background noise level of the local environment from the signals detected by microphone 711 and sets the gain of microphone 711 to a level selected to compensate for the natural tendency of the user of the mobile terminal 701.

The CODEC 713 includes the ADC 723 and DAC 743. The memory 751 stores various data including call incoming tone data and is capable of storing other data including music data received via, e.g., the global Internet. The software module could reside in RAM memory, flash memory, registers, or any other form of writable computer-readable storage medium known in the art including non-transitory computer-readable storage medium. For example, the memory device 751 may be, but not limited to, a single memory, CD, DVD, ROM, RAM, EEPROM, optical storage, or any other non-volatile or non-transitory storage medium capable of storing digital data.

An optionally incorporated SIM card 749 carries, for instance, important information, such as the cellular phone number, the carrier supplying service, subscription details, and security information. The SIM card 749 serves primarily to identify the mobile terminal 701 on a radio network. The card 749 also contains a memory for storing a personal telephone number registry, text messages, and user specific mobile station settings.

While features have been described in connection with a number of embodiments and implementations, various obvious modifications and equivalent arrangements, which fall within the purview of the appended claims are envisioned. Although features are expressed in certain combinations among the claims, it is contemplated that these features can be arranged in any combination and order.

We claim:

1. A computer-implemented method of determining a route for mood improvement, the method comprising:
   determining, by an autonomous vehicle from one or more sensors that enable the autonomous vehicle to determine a mood of an individual from measurements tied to one of a blood pressure measurement of the individual, a temperature measurement of the individual, movement data of the individual, or a combination thereof, the mood of the individual;
   receiving, by the autonomous vehicle, a destination as an input;
   determining, by the autonomous vehicle, a route from a current location of the individual to the destination via a plurality of road segments for improving the mood of the individual, wherein determining the mood of the individual is based on an analysis of a mobility pattern of the individual and a baseline mood of the individual for each day of a week; and controlling, by the autonomous vehicle, to follow the route from the current location of the individual to the destination via at least one of the plurality of road segments.

2. The method of claim 1, wherein identification of one or more road segments of the plurality of road segments to be part of the route is based on mood data associated with the one or more road segments.

3. The method of claim 2, wherein the mood data associated with the one or more road segments is based on one or more visual aspects associated with the one or more road segments.

4. The method of claim 1, wherein determining the mood of the individual is based on one or more metrics of the individual captured via one or more sensors.

5. The method of claim 1, further comprising: based on the determined route, determining the autonomous vehicle for transporting the individual from the current location to the destination.

6. The method of claim 5, wherein determining the autonomous vehicle for transporting the individual from the current location to the destination further comprises: determining autonomous vehicle level data associated with one or more aspects of the determined route.

7. The method of claim 5, wherein determining the autonomous vehicle for transporting the individual from the current location to the destination further comprises: analyzing one or more attributes of one or more autonomous vehicles; and based on the determined route and the analysis of the one or more attributes of the one or more autonomous vehicles, selecting an autonomous vehicle from the one or more autonomous vehicles.

8. An apparatus for determining a route for mood improvement, the apparatus comprising:
a processor; and
a memory comprising computer program code for one or more programs, wherein the memory and the computer program code is configured to cause the processor of the apparatus to:
determine, by an autonomous vehicle from one or more sensors that enable a device to determine a mood of an individual from measurements tied to one of a blood pressure measurement of the individual, a temperature measurement of the individual, movement data of the individual, or a combination thereof, the mood of the individual;
receive, by the autonomous vehicle, a destination as an input;
determine, by the autonomous vehicle, a route from a current location of the individual to the destination via a plurality of road segments for improving the mood of the individual, wherein the computer program code is configured to cause the processor of the apparatus to determine the mood of the individual further causes the processor of the apparatus to analyze a mobility pattern of the individual and a baseline mood of the individual for each day of a week; and
controlling, by the autonomous vehicle, to follow the route from the current location of the individual to the destination via at least one of the plurality of road segments.

9. The apparatus of claim 8, wherein identification of one or more road segments of the plurality of road segments to be part of the route is based on mood data associated with the one or more road segments.

10. The apparatus of claim 9, wherein the mood data associated with the one or more road segments is based on one or more visual aspects associated with the one or more road segments.

11. The apparatus of claim 8, wherein the computer program code is configured to cause the processor of the apparatus to determine the mood of the individual further causes the processor of the apparatus to analyze one or more metrics of the individual captured via one or more sensors.

12. The apparatus of claim 8, wherein the computer program code is configured to further cause the processor of the apparatus to, based on the determined route, determine the autonomous vehicle for transporting the individual from the current location to the destination.

13. The apparatus of claim 12, wherein the computer program code is configured to cause the processor of the apparatus to determine the autonomous vehicle for transporting the individual from the current location to the destination further causes the processor of the apparatus to determine autonomous vehicle level data associated with one or more aspects of a route for transporting the individual.

14. The apparatus of claim 12, wherein the computer program code is configured to cause the processor of the apparatus to determine the autonomous vehicle for transporting the individual from the current location to the destination further causes the processor of the apparatus to: analyze one or more attributes of one or more autonomous vehicles; and based on the determined route and the analysis of the one or more attributes of the one or more autonomous vehicles, select an autonomous vehicle from the one or more autonomous vehicles.

15. A non-transitory computer-readable storage medium comprising one or more instructions for execution by one or more processors of a device, the one or more instructions which, when executed by the one or more processors, cause the device to:
determine, by an autonomous vehicle, from one or more sensors that enable a device to determine a mood of an individual from measurements tied to one of a blood pressure measurement of the individual, a temperature measurement of the individual, movement data of the individual, or a combination thereof, the mood of the individual;
receive, by the autonomous vehicle, a destination as an input;
determine, by the autonomous vehicle, a route from a current location of the individual to the destination via a plurality of road segments for improving the mood of the individual, wherein the instructions to cause the device to determine the mood of the individual further causes the device to analyze a mobility pattern of the individual and a baseline mood of the individual for each day of a week; and
controlling, by the autonomous vehicle, to follow the route from the current location of the individual to the destination via at least one of the plurality of road segments.

16. The non-transitory computer-readable storage medium of claim 15, wherein identification of one or more road segments of the plurality of road segments to be part of the route is based on mood data associated with the one or more road segments.

17. The non-transitory computer-readable storage medium of The non-transitory computer-readable storage medium of wherein the one or more instructions which, when executed by the one or more processors, further cause the device to based on the determined route, determine the autonomous vehicle for transporting the individual from the current location to the destination.

18. The non-transitory computer-readable storage medium of claim 17, wherein the one or more instructions which, when executed by the one or more processors, cause the device to determine the autonomous vehicle for transporting the individual from the current location to the destination further cause the device to: analyze one or more attributes of one or more autonomous vehicles; and based on the determined route and the analysis of the one or more attributes of the one or more autonomous vehicles, select an autonomous vehicle from the one or more autonomous vehicles.

\* \* \* \* \*